United States Patent [19]

Burke

[11] Patent Number: 4,650,934

[45] Date of Patent: Mar. 17, 1987

[54] HAND MOVEMENT CONTROLLER

[76] Inventor: Patrick G. Burke, P.O. Box 129, Tumbler Ridge, B.C., Canada, V0C 2W0

[21] Appl. No.: 772,112

[22] Filed: Sep. 3, 1985

Related U.S. Application Data

[63] Continuation-in-part of Ser. No. 669,546, Nov. 8, 1984, abandoned.

[51] Int. Cl.$^4$ ............................................. H01H 13/70
[52] U.S. Cl. .................................... 200/5 R; 200/5 A
[58] Field of Search ...................... 200/5 R, 5 A, 6 A; 235/145 R; 178/17 C; 179/90 K; 400/472, 473, 476, 481–489, 492, 682

[56] References Cited

U.S. PATENT DOCUMENTS

| | | | |
|---|---|---|---|
| 2,863,010 | 12/1958 | Riedl | 200/5 R |
| 3,005,055 | 10/1961 | Mattke | 179/90 K |
| 3,022,878 | 2/1962 | Seibel et al. | 400/479 |
| 3,879,586 | 4/1975 | DuRocher et al. | 200/5 A |
| 3,965,315 | 6/1976 | Wuenn | 200/6 A |
| 4,046,975 | 9/1977 | Seeger, Jr. | 200/5 A |
| 4,065,650 | 12/1977 | Lou | 200/5 R |
| 4,256,931 | 3/1981 | Palisek | 200/5 A |
| 4,360,892 | 11/1982 | Endfield | 178/17 C X |
| 4,385,215 | 5/1983 | Lemberg | 200/5 A |
| 4,433,217 | 2/1984 | Griffith | 200/5 R |
| 4,458,114 | 7/1984 | May | 200/6 A |
| 4,465,908 | 8/1984 | Griffith et al. | 200/5 R |
| 4,517,424 | 5/1985 | Kroczynski | 235/145 R X |
| 4,540,865 | 9/1985 | Calder | 200/5 A X |

FOREIGN PATENT DOCUMENTS

| | | | |
|---|---|---|---|
| WO84/00518 | 2/1984 | PCT Int'l Appl. | 400/489 |
| 1016993 | 1/1966 | United Kingdom | 400/489 |
| 1480243 | 7/1977 | United Kingdom | |
| 2076743A | 12/1981 | United Kingdom | |
| 2131746A | 6/1984 | United Kingdom | |

OTHER PUBLICATIONS

IBM Tech. Disc. Bull.; J. Greenfield et al.; "Keyboard Assembly", vol. 25, No. 8, Jan., 1983 pp. 4265–4267.
IBM Tech. Disc. Bull.; R. Seibel et al.; "Keyboard", vol. 3, No. 6, Nov., 1960, p. 16.
Xerox Disclosure Journal; D. C. Kowalski; "Semi-Captive Keyboard", vol. 1, No. 2, Feb. 1976, p. 85.

Primary Examiner—J. R. Scott
Attorney, Agent, or Firm—Hirons, Rogers & Scott

[57] ABSTRACT

A hand movement controller is described which permits a variety of control functions to be performed by single left or right handed operation, and is particularly suitable for handicapped persons. The controller comprises a base which is generally wedge-shaped in side elevation with a sloping top surface on which is located a movable palm support on which the hand rests. One or two rows of keys are symmetrically spaced about the front edge of the palm support for engagement by the fingers of the hand. The distance between the movable palm support and keys is adjustable so that it can support the fingers to permit them to pivot freely about the knuckles with minimal strain over a prolonged period of time. The spacing of the row or rows of keys about the palm support is designed to optimize reaction time for fast operation. In a preferred embodiment an outer row of five keys and an inner row of three keys are used and permit control of movement in three dimensions. The palm support can be moulded from a plastic thermoplastic material to be custom suited to the individual.

12 Claims, 6 Drawing Figures

HAND MOVEMENT CONTROLLER

This application is a continuation-in-part of U.S. patent application Ser. No. 669,546 filed Nov. 8, 1984 now abandoned.

FIELD OF THE INVENTION

The present invention relates to a hand movement controller and particularly, but not exclusively, to a hand movement controller for use by the handicapped and the like which provides support and comfort for the operator's hand and permits free movement of the fingers to operate a plurality of keys or control switches.

REVIEW OF THE PRIOR ART

A hand movement controller should satisfy a number of basic design criteria in addition to being inexpensive, aesthetic and usable by only one hand. The controller should cause very little strain on the hand and arm and should provide support and comfort for the palm so that prolonged use can be made of the controller without fatigue. In addition, the keys actuatable by fingers should be positioned so that very little stretching is needed to engage them, and so minimize reaction time by taking advantage of fastest possible reactions of the user. Also the palm support should be movable to so that different hand sizes can easily be accomodated. The device should be capable of use with either hand, and the fingers should be able to be supported and moved independently of the rest of the hand and arm, so that tension in the hand or arm does not affect movement of the fingers or reaction time. Also, such a hand movement controller should be able to be simply made, should accommodate circuitry and wiring for connection to controllable equipment, and should be lightweight and easily carried by the user.

Perhaps the most well-known type of hand movement controller is the joy-stick commonly used for television-type video games. Joy-sticks have several substantial disadvantages which mitigate against their widespread use as a general hand movement controller. Firstly, two hands are usually required to operate the joy-stick; one hand to hold the base and the other to move the stick relative to the base. Secondly, the joy-stick usually involves some relatively complex manufacturing construction by using rotary potentiometers to sense the direction of movement. Furthermore, when holding a joy-stick, the hand moving the lever is usually gripped on the top of the palm support portion of the stick and, the arm is tensed to support the hand, which after short periods of time causes fatigue and strain. Joy-stick instruments are generally unsuitable for the handicapped and for a hand movement controller which is to be used for a considerable period of time.

Other types of hand movement controllers have been proposed, for example U.S. Pat. No. 2,863,010 to Riedl which issued in 1958 discloses a switch which can be activated by the pushing of a single plate. This construction was extremely simple and one, two or three switches could be actuated by controlling the direction of pushing on the plate. This switch was designed for wall mounted use and is unsuitable for use a general hand movement controller.

U.S. Pat. No. 3,022,873 to Seibel et al and assigned to I.B.M. discloses a communication device which looks like an oversize glove into which the hand would fit and each finger and thumb would engage a separate switch. The hand was supported in the housing by palm support 3. This device was exceedingly cumbersome and complex, and in order to be able to operate it the hand would firstly have to be inserted through an aperture into the device and then the fingers engaged in respective switch apertures, a feat which would be very difficult for the handicapped. Although single hand operation was possible with this device there was no palm support and the fingers were constrained in recesses for the respective switches.

A semi-captive keyboard was disclosed in Xerox Disclosure Journal, Volume 1, Number 2, dated February 1976, in which the palm was supported on a generally flat base and the fingers and thumb inserted through apertures in an elevated front portion of the base to engage clusters of keys. A switch was also located underneath the palm. With this device many limitations were present, for example the construction of the key clusters was complex and there was no support for the palm. This meant that the fingers were elevated slightly above the back of the palm which caused undue strain in the back of the hand and in the arm, leading to rapid fatigue. In addition, the fingers again have to be inserted into separate apertures and engaged therein, a manipulation not easily accomplished by the handicapped.

U.S. Pat. No. 4,465,908 to Griffith et al issued 14th August 1984 and relates to a hand controller for use in controlling the motion of a cursor on a video display comprising a spherical surface on which is mounted a flat plate. The bottom of the flat plate has an electrical switch which indicates the direction in which the flat plate is rocking over the spherical surface. The flat plate is spring-loaded so that in the absence of the rocking force, a restoring force is generated to return the flat plate to its original position. In a preferred embodiment the controller is capable of moving a cursor in eight different directions. No finger-operated buttons are provided and this device responds to movement of the hand and not of the fingers, thus limiting the control possible with such a device. This is because the fingers generally have the fastest reaction time of any part of the body and also are the most sensitive and easy to execute complex control instructions rapidly.

British Patent Application No. 2076743A published Dec. 9, 1981 relates to an input device for generating characters. However there is no disclosure of a movable palm support and the device is only suitable for use by one hand, in the case illustrated the right hand. This device cannot readily accomodate different sized hands and requires a custom unit for each user. Also different units require to be made for left-handed individuals. This leads to increased costs of production.

DEFINITION OF THE INVENTION

An object of the present invention is to provide a hand movement controller which obviates or mitigates the disadvantages associated with the aforementioned prior art hand movement controllers.

Accordingly, in one aspect of the invention there is provided a hand movement controller for operation by a single hand and having a movable elevated palm support and a plurality of keys for actuation by the fingers of either hand, the palm support supporting the fingers in such a position to permit free movement of the fingers without undue hand or arm movement.

In a preferred embodiment of the invention sufficient keys are provided to permit control of three-dimensional movement and the movable palm support is designed to have three-dimensional topography to fit into the natural cavity formed in the palm of a hand when resting it on a flat surface. In an alternative embodiment of the invention a minimum number of keys are provided to enable two-dimensional control to be achieved using the hand controller.

DESCRIPTION OF THE DRAWINGS

These and other aspects of the present invention will be described by way of example, with reference to the accompanying drawings, in which.

DESCRIPTION OF THE PREFERRED EMBODIMENTS

Figure 1:
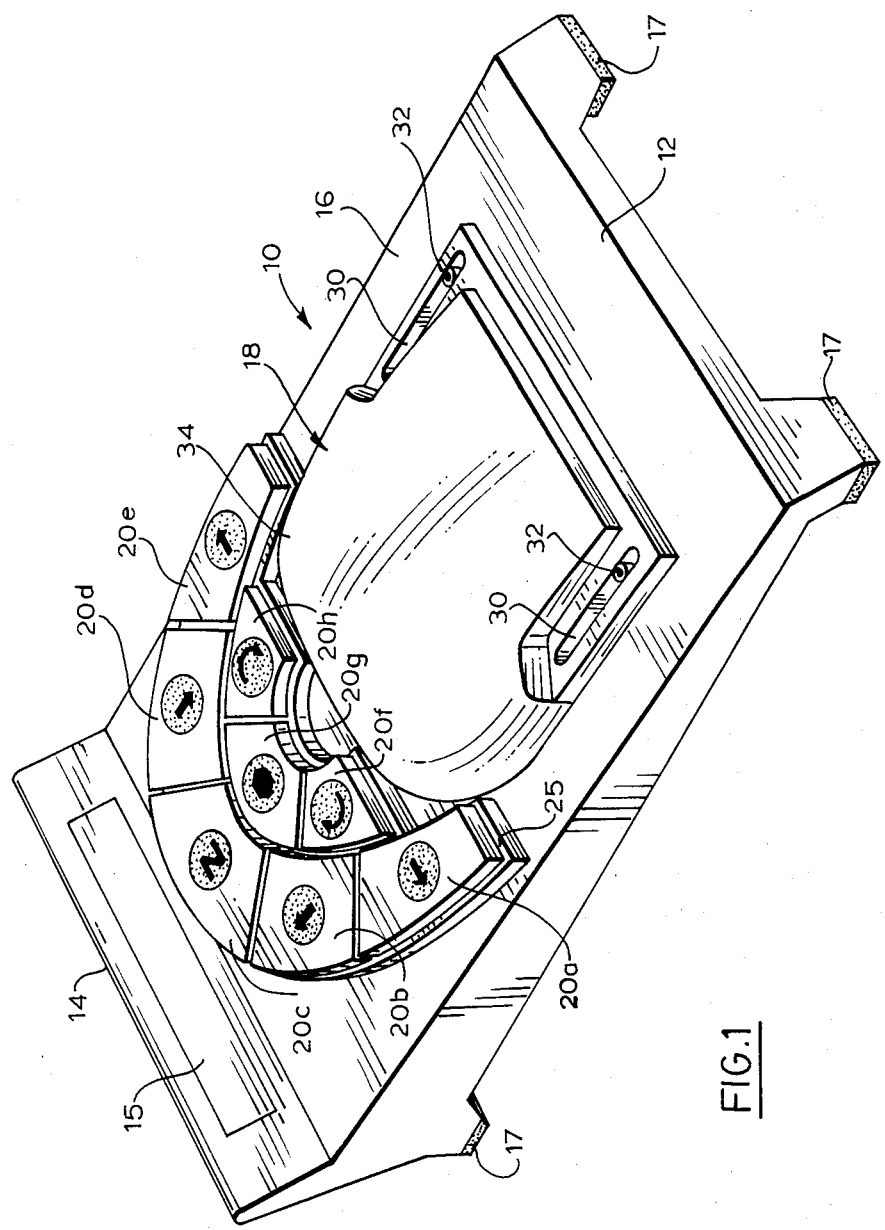
FIG. 1 is a perspective view from above of a preferred embodiment of a hand movement controller in accordance with the present invention.

Reference is first made to FIGS. 1-5 of the drawings which show a preferred form of a hand movement controller. The controller consists of a generally rectangular base 10 about 15.5 cm. wide by 23 cm. long which is generally wedge-shaped in side elevation having a lower front portion 12 about 1 cm. high and a higher rear portion 14 about 2½ cm. high. The rear portion 14 provides a surface 15 on which information can be displayed, such as a logo. The base is hollow and contains switch circuitry on a printed circuit to permit transmission of electrical signals upon operation of keys located on the wedge-shaped base, as will be later explained. The base has four non-slip feet 17 at its corners which ensure minimum movement of the device during operation. On the top surface 16 there is mounted an elevated movable palm support 18 which is designed to fit into the palm recess when the operator's hand is resting thereon in normal relaxed extended postion, so as to support the palm and fingers and to permit the fingers to pivot freely about the knuckles without movement of the hand or the respective arm. Eight keys indicated by reference numerals 20a through 20h are located in proximity to the rear of the device for actuation by the fingers with the hand in this position. The keys are arranged in inner and outer parallel arcuate rows concave toward the palm support and are resiliently biased upward in a normal 'off' position. The outer arcuate row has five keys 20a through 20e which are each arcuate in shape, as seen in plan, arranged symmetrically in the arc about the centre key, and these can all be engaged by respective fingers or the thumb of either the left or right hand. The inner arcuate row has three keys 20f through 20h adjacent the three centre keys 20b, 20c and 20d of the outer row, so that the three centre fingers can move between these six keys to give a variety of hand movement control signals, as will be explained. A ledge 25 surrounds the keys to prevent small objects from getting under the keys.

Figure 2:
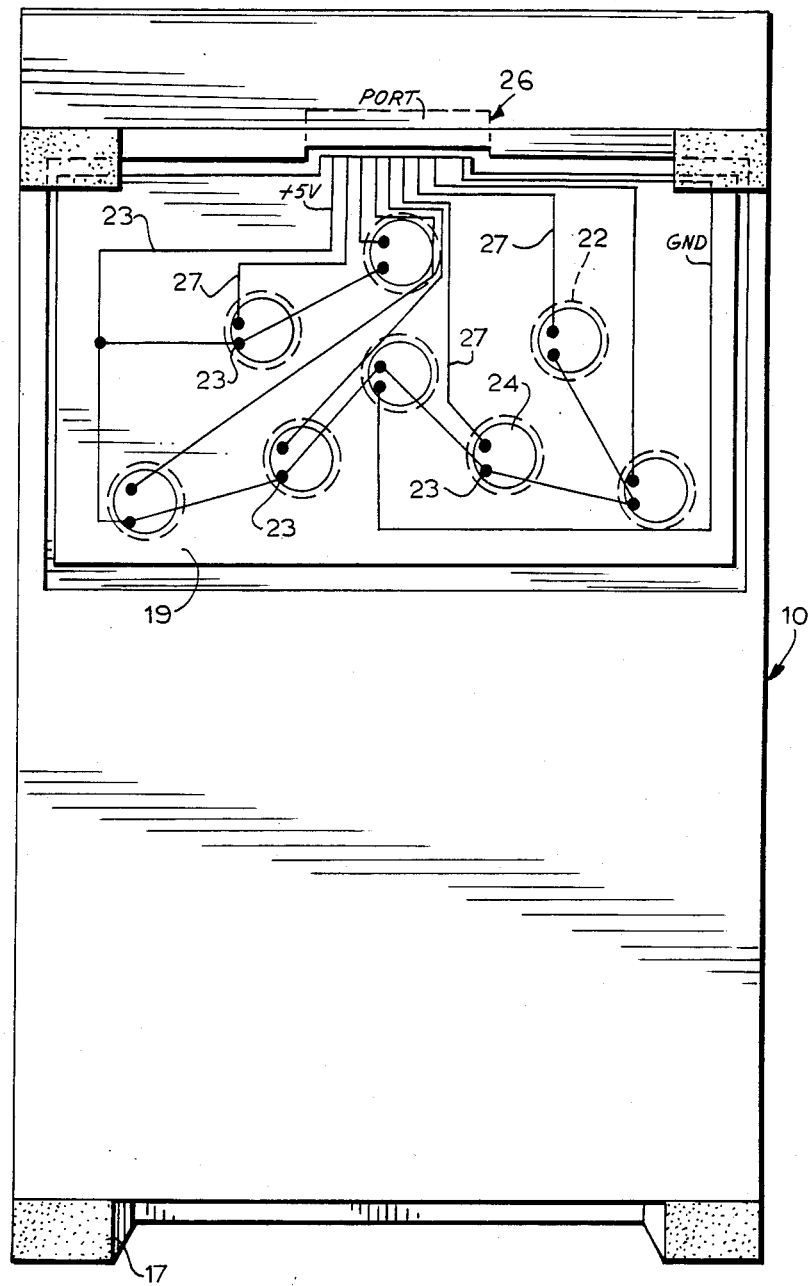
FIG. 2 is a bottom view of the underside of the controller shown in FIG. 1 with a cover plate removed to show switch connections.

FIG. 2 shows an underneath view of the hand movement controller with a circuit board cover shown removed to reveal a circuit board 19. The underside 22 of each key 20 is electrically conductive and contacts a respective switch area 24 on the circuit board. Each switch area receives terminals of two conductors 23 and 27 which are normally disconnected. The conductor 23 is common to all the switches and has a potential thereon of +5 v, while the other conductors 27 are separate for each switch and have a lower potential. The control signals are taken from the circuit board out through female plug port 26 located at the rear of the unit and best seen in FIG. 5.

When a key is depressed, the respective conductive underside 22 thereof connects the respective conductors 23 and 27 so that a respective electrical signal is sent to port 26. The centre key 20g in the inner arcuate row has its other conductor 27 connected to a ground and this is a stop key. Actuation of the stop key disables all the other keys by grounding them and allows the user to choose, while they are thus disabled, a combination of the other keys to effect movement of the controlled object in a particular selected direction. Releasing the stop key 20g engages the software to move the controlled object in that selected direction.

Figure 3:
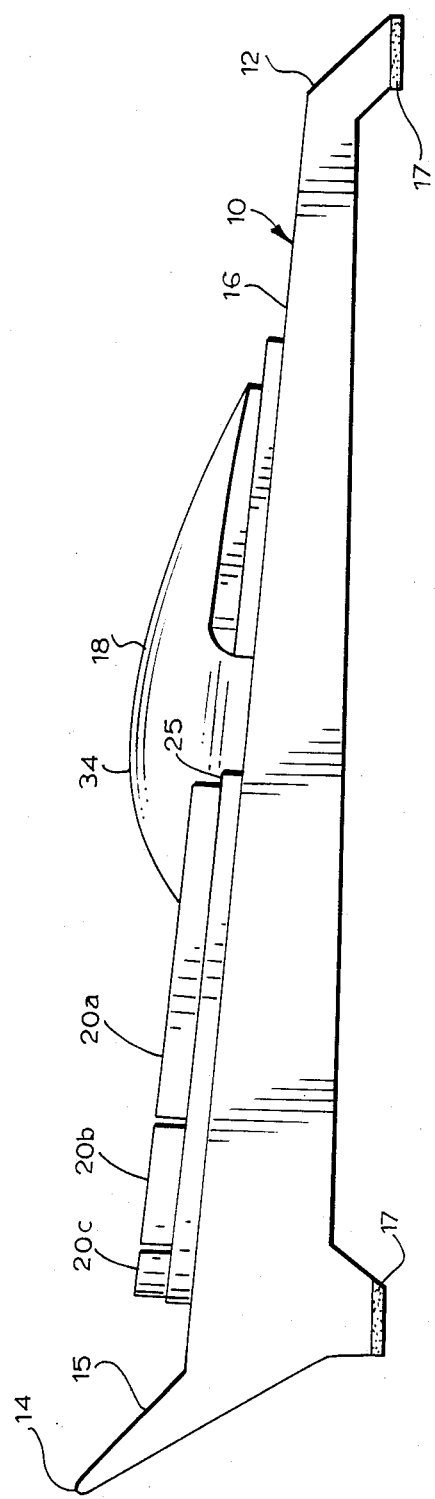
FIG. 3 is a side elevation of the controller of FIG. 1.
Figure 4:
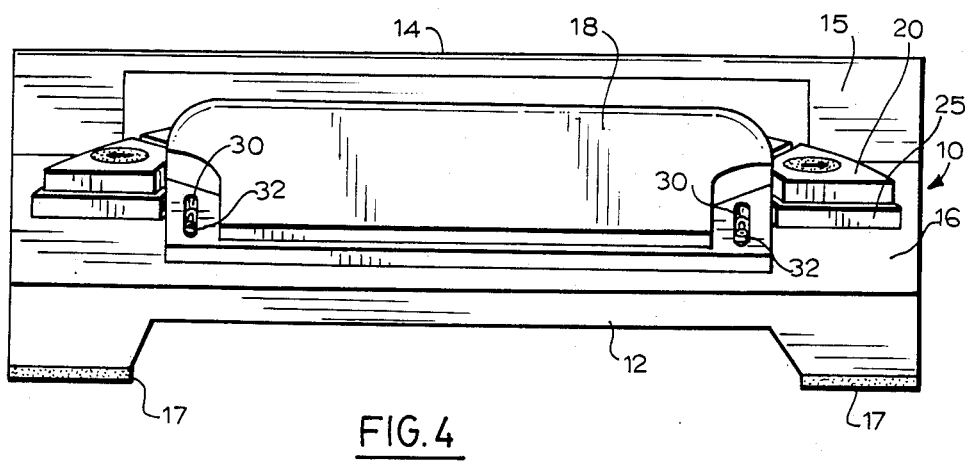
FIGS. 4 and 5 are respective front and back end elevations of the controller of FIG. 1.
Figure 5:
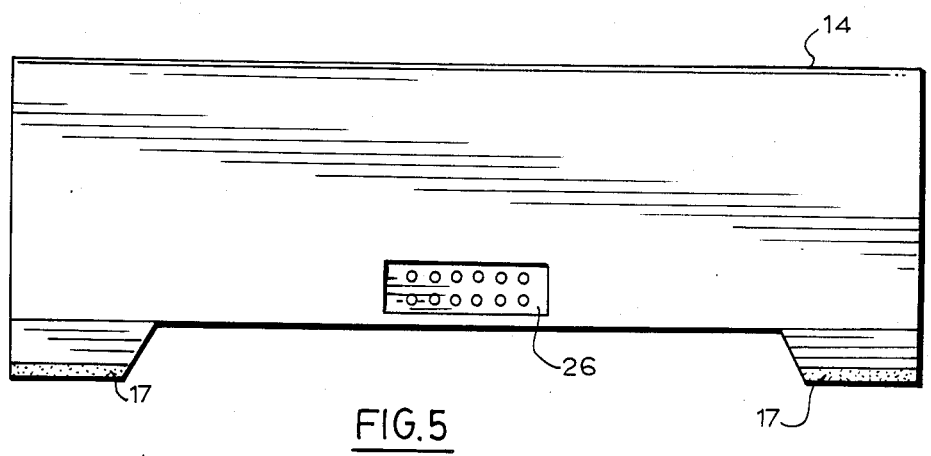

Reference is now made to FIG. 3 which is a side elevational view of the hand movement controller and shows the movable palm support 18 upwardly convex to fit into the palm and elevated above the surface 16. FIG. 3 together with FIG. 1 also shows the elongated shape of the two endmost keys 20a and 20e of the outer arcuate row longitudinally of the base 16, so that either key can be readily engaged by either the little finger of the thumb of a hand, depending upon which hand is being used, despite the considerable difference in longitudinal placement on the average hand of those two digits. It will be appreciated that the surface 16 and the palm support 18 are usually in practice made from a moulded material and can be custom fitted to suit each individual hand. This is particularly advantageous of handicapped or arthritic persons whose hands and fingers frequently are deformed as a symptom of their illness. However the palm support 18 shown is of a standard shape and has longitudinal grooves 30 which allow the support to be moved towards and away from the keys to permit adjustment of the palm support-key distance to suit different hand sizes. Releasable fasteners 32 are provided to hold the support in the desired position.

It will be appreciated that the keys are positioned so as to be engaged by the fingertips with the hand in extended relatively relaxed position without undue stretching of the fingers. That is, when the hand is at rest each finger can rest on a particular key button and the finger-engaged surfaces thereof are concave upward to minimise finger slippage. This positioning has the advantage of making reaction time very quick and accordingly the selection and the location of the required direction control key or keys is carried out to take full advantage of normal reaction sensing. For example, the leftmost key button 20a is used to obtain left-wise movements and has an arrow indicating the direction left; to go left one would normally react by pressing that key. The arrangement of the keys in this manner further reaction time and improves speed of operation and control of movement.

In use, for example, the hand movement controller is located on a flat surface and an electric connecting cord is connected between the controller and a display unit with a screen on which a cursor is to be controlled. The heel of the hand is then laid on the surface 16 so that the palm support 18 lies in the palm of the hand and the high area 34 supports the bridge of the palm allowing the fingers to move easily. Each finger and the thumb is automatically located adjacent to a suitable combination of keys. The leftmost key 20a of the outer arcuate row is used to produce left movement and the rightmost key 20e right movement of the cursor. The outer top keys 20b and 20d can be used to move a cursor or an object up or down respectively, while the centre top key 20c can be used to actuate a switch as a 'fire' key or perform another programmed function when cursor movement produced by the other keys is complete. The three inner row keys 20f to 20h are used for three-dimensional control of the display, for example the inner left and inner right key 20f and 20h can move the cursor at right angles to the plane of movement controlled by the outer row keys, while the inner centre key 20g is the stop key which functions as described above.

It will be appreciated that the major advantage of this structure is that the palm is supported and the fingers are free to pivot without requiring any movement or adjustment of the hand or arm. Because the fingers alone are used to actuate the keys many spontaneous movements can be made without the fingers becoming tired and consequently the reaction time using the movement controller is much superior than with the prior art devices. Also, because the unit is operable by a single hand this leaves the other hand free to do other tasks or, in the case of handicapped people, it has the advantage that only one hand could be used to move an object in three-dimensions and then control actuation of the object. The arrangement of keys on the surface 16 is also advantageous because both left-handed and right-handed persons can use it to take advantage of normal reactions, thus further reducing reaction time. Because the movable palm support 18 and base 10 are made from a moulded material the device can be custom fitted to each individual's hand and the strain in the hand or arm can be minimized because of the support and comfort provided by the movable palm support being moved to, and secured at, a desired position. Therefore there is no tension in the arm or hand which can be transmitted to the fingers and which could affect control even during tense situations. Also, because the fingers are freely movable they are unlikely to get tired which is the principle cause of increased reaction time and errors.

Figure 6:
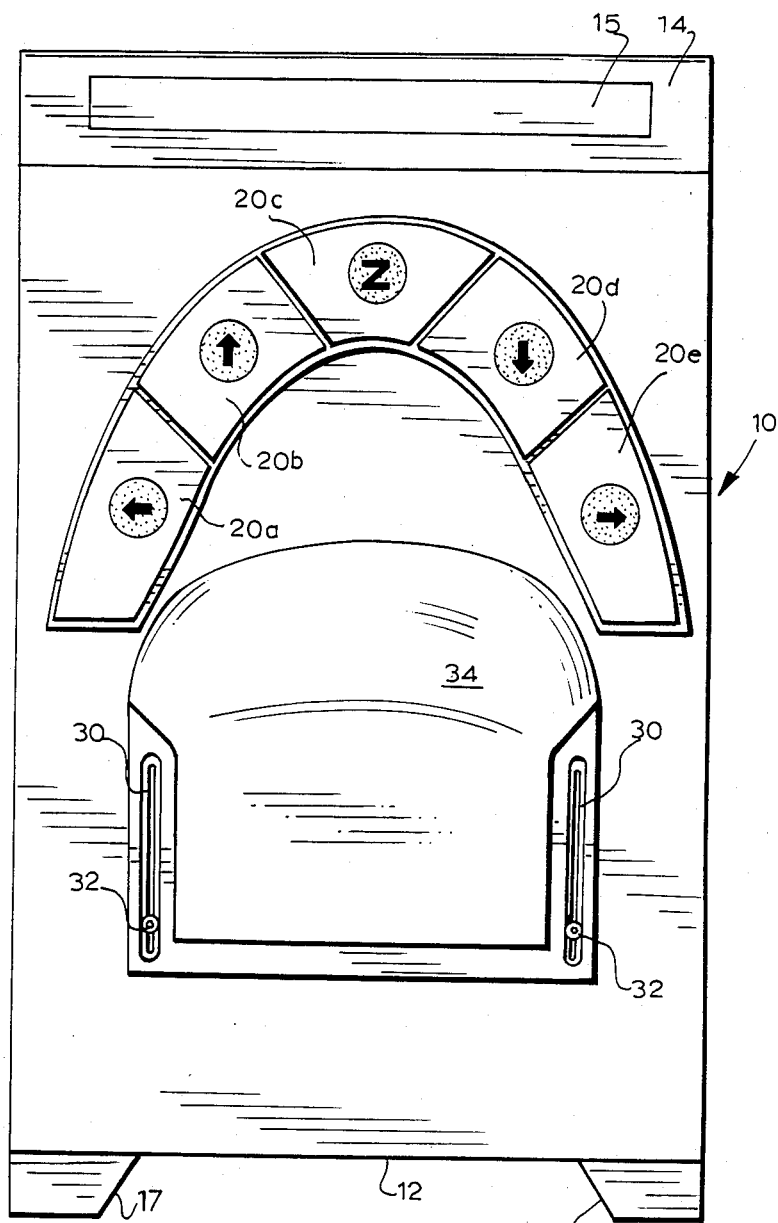
FIG. 6 is a perspective view similar to FIG. 1 of a hand movement controller which is an alternative embodiment of the invention.

Reference is now made to FIG. 6 which shows an alternative embodiment in which a row of only five outer keys 20a to 20e are required to permit two-dimensional movement to be controlled by the controller. The five keys permit left, right (keys 20a and 20e) and up, down (keys 20b and 20d) movement with the fifth key 20e available to control actuation when the object being moved is at a desired location. Although this controller may be suitable for moving an object or cursor on a screen, its use in the three-dimensional environment is limited because the movement is necessarily restricted to be in a single plane and for this reason the preferred eight key embodiment is more suitable for the handicapped, who usually have to deal with real three-dimensional situations. The two-dimensional version is eminently suitable for playing video games and controlling graphics of a cursor on a screen and the like.

It will be appreciated that various modifications may be made to the embodiments hereinbefore described without departing from the scope of the invention. For example, the number of keys can be varied depending on the functional requirements of the task to be performed. For example, the keys could be made to arrange to control rotation in certain directions and movements diagonally in others, depending on the particular functions involved. Also, it will be appreciated that the unit need not use a cable hardware connection and instead telemetry, or an infrared beam, or a laser beam could be used to relay the fact that particular keys have been actuated thus eliminating the need for a connecting cord. The device could be also used to control a robot arm.

Advantages of the invention are that it is inexpensive, portable and relatively simple to construct. In addition it only requires single left or right handed operation and can be used for a long period of time without generating fatigue by users having different sized hands.

I claim:

1. A hand movement controller comprising:
   a base having a rear portion and a front portion and an upper surface between the front and rear portions;
   an elevated palm support movably mounted on the base upper surface to extend upwardly therefrom, the palm support having a support upper surface on which rests the palm of either a right or left hand in extended relaxed position;
   a first row of five switch keys mounted on the base between the said rear portion and the palm support, the row being arcuate as seen in plan from above, symmetrically disposed about the centre key, and concave toward the palm support, for engagement by the fingers and the thumb of either a right hand or a left hand resting on the palm support;
   means mounting the palm support on the base for longitudinal movement toward and away from the said arcuate row of keys for selection by said longitudinal movement of the spacing between the support and the keys to accommodate fingers of different lengths, and so that the fingers and the thumb engage all the keys in the row with the hand in said extended relaxed position and movable freely about the knuckles without longitudinal movement of the hand on the palm support; and
   means for fastening the palm support to the base with the selected spacing between the support and the keys.

2. A controller as claimed in claim 1, wherein the two outermost keys are elongated in longitudinal direction between the front end rear portions to provide engagement therewith by either the little finger or the thumb of either hand despite the different longitudinal placement thereof on the human hand.

3. A controller as claimed in claim 1, and including a second row of three keys mounted on the base between the first row and the palm support, the second row also being arcuate as seen in plan and concave toward the palm support.

4. A controller as claimed in claim 3, wherein the three keys of the second row are disposed respectively adjacent the three middle keys of the first row for engagement by the same respective finger for operation thereof.

5. A controller as claimed in claim 2, and including a second row of three keys mounted on the base between the first row and the palm support, the second row also being arcuate as seen in plan and concave toward the palm support.

6. A controller as claimed in claim 5, wherein the three keys of the second row are disposed respectively adjacent the three middle keys of the first row for engagement by the same respective finger for operation thereof.

7. A controller as claimed in claim 1, wherein the palm support is upwardly convex tapering slowly with progressively increasing thickness from the base front to a maximum thickness and tapering more quickly with decreasing thickness from the maximum thickness toward the base rear.

8. A controller as claimed in claim 1, wherein the said base is wedge-shaped in longitudinal cross-section increasing in thickness from said front portion to said rear portion with its said upper surface sloping upward.

9. A controller as claimed in claim 1, wherein all of the keys have a common conductor and a respective individual conductor, operation of a key connecting its respective conductor to the common conductor, and wherein a centre key of the row is a stop key having its respective conductor connected to ground so that operation of that key will connect all of the keys to ground.

10. A controller as claimed in claim 5, wherein the centre key of the second row is a stop key having its respective conductor connected to ground so that operation of that key will connect all of the keys to ground.

11. A controller as claimed in claim 1, wherein the two outermost keys of the first row have thereon indicia representing two opposite directions of movement of a first direction, the two keys respectively adjacent the two outermost keys have thereon indicia representing two opposite directions of movement of a second direction transverse to the said first direction, and the remaining centre key has thereon an indice representing a function independent of movement direction.

12. A controller as claimed in claim 5, wherein the two outermost keys of the first row have thereon indicia representing two opposite directions of movement of a first direction, the two keys respectively adjacent the two outermost keys have thereon indicia representing two opposite directions of movement of a second direction transverse to the said first direction, and the remaining centre key has thereon an indice representing a function independent of movement direction, and wherein the two outermost keys of the second row have thereon indicia representing two opposite directions of movement of a third direction transverse to both said first and second directions, and the remaining centre key of the second row has thereon an indice representing a stop function for disabling of the other keys when actuated.

* * * * *